United States Patent
Chambon et al.

(10) Patent No.: US 8,835,694 B2
(45) Date of Patent: Sep. 16, 2014

(54) PROCESS FOR TRANSFORMATION OF LIGNOCELLULOSIC BIOMASS OR CELLULOSE BY CATALYSTS BASED ON TIN OXIDE AND/OR ANTIMONY OXIDE AND A METAL THAT IS SELECTED FROM THE GROUPS 8 TO 11

(75) Inventors: Flora Chambon, Bron (FR); Nadine Essayem, Saint Just Chaleyssin (FR); Franck Rataboul, Lyons (FR); Catherine Pinel, Lyons (FR); Amandine Cabiac, Givors (FR); Emmanuelle Guillon, Vourles (FR)

(73) Assignees: Centre National de la Recherche Scientifique, Paris (FR); IFP Energies Nouvelles, Rueil Malmaison Cedex (FR)

( * ) Notice: Subject to any disclaimer, the term of this patent is extended or adjusted under 35 U.S.C. 154(b) by 0 days.

(21) Appl. No.: 13/995,518

(22) PCT Filed: Dec. 16, 2011

(86) PCT No.: PCT/FR2011/000662
§ 371 (c)(1),
(2), (4) Date: Jun. 28, 2013

(87) PCT Pub. No.: WO2012/085362
PCT Pub. Date: Jun. 28, 2012

(65) Prior Publication Data
US 2013/0281741 A1   Oct. 24, 2013

(30) Foreign Application Priority Data
Dec. 22, 2010   (FR) ..................... 10 05023

(51) Int. Cl.
C07C 45/60 (2006.01)
C07C 29/14 (2006.01)
C07C 29/132 (2006.01)

(52) U.S. Cl.
CPC .............. *C07C 45/60* (2013.01); *C07C 29/132* (2013.01)

USPC ............................... 568/386; 568/863

(58) Field of Classification Search
USPC ................................ 568/386, 863
See application file for complete search history.

(56) References Cited

U.S. PATENT DOCUMENTS

| | | | |
|---|---|---|---|
| 2,488,722 A | 11/1949 | Gurkan | |
| 5,354,914 A | 10/1994 | Gubitosa et al. | |
| 5,496,786 A | 3/1996 | Gubitosa et al. | |
| 2011/0319672 A1 | 12/2011 | Liu et al. | |

FOREIGN PATENT DOCUMENTS

WO   2010101637 A2   9/2010

OTHER PUBLICATIONS

International Search Report from PCT/FR2011/000662 dated Feb. 9, 2012.
Tian Yin Deng, et al. "Cellulose conversion to polyols on supported Ru catalysts in aqueous basic solution" Science China Chemistry, vol. 53, No. 7, [Jul. 2010], pp. 1476-1480.
Regina Palkovits, et al. "Hydrogenolysis of cellulose combining mineral acids and hydrogenation catalysts" Green Chemistry, Royal Society of Chemistry, vol. 12, No. 6, [2010], pp. 972-978.
Ken-ichi Shimizu, et al. "Effects of Bronsted and Lewis acidities on activity and selectivity of heteropolyacid-based catalysts for hydrolysis of cellobiose and cellulose" Green Chemistry, Royal Society of Chemistry, vol. 11, No. 10, [2009], pp. 1627-1632.
Tushar P. Vispute, et al. "Production of hydrogen, alkanes and polyols by aqueous phase processing of wood-derived pyrolysis oils" Green Chemistry, Royal Society of Chemistry, vol. 11, No. 9, [2009], pp. 1433-1445.

*Primary Examiner* — Sikarl Witherspoon
(74) *Attorney, Agent, or Firm* — Millen, White, Zelano, Branigan, P.C.

(57) ABSTRACT

The invention relates to a process for transformation of lignocellulosic biomass or cellulose using heterogeneous catalysts that are based on tin oxide and/or antimony oxide, dispersed on a substrate and containing at least one element in the particular metal state. The use of these catalysts makes it possible to obtain directly upgradable products, in particular hydroxyacetone and propylene glycol with high selectivity.

16 Claims, No Drawings

US 8,835,694 B2

PROCESS FOR TRANSFORMATION OF LIGNOCELLULOSIC BIOMASS OR CELLULOSE BY CATALYSTS BASED ON TIN OXIDE AND/OR ANTIMONY OXIDE AND A METAL THAT IS SELECTED FROM THE GROUPS 8 TO 11

FIELD OF THE INVENTION

The invention relates to a process for transformation of lignocellulosic biomass or cellulose directly into upgradable products and in particular into hydroxyacetone and into propylene glycol using heterogeneous catalysts.

PRIOR ART

For several years, there has been a very sharp resurgence of interest for the incorporation of products of renewable origin within the fuel and chemistry branches, in addition to or in place of products of fossil origin. One possible method is the conversion of cellulose, contained in the lignocellulosic biomass, into chemical products or intermediate products, and in particular into hydroxyacetone and into propylene glycol.

The term lignocellulosic biomass (BLC) or lignocellulose encompasses several products that are present in variable quantities according to the origin thereof: cellulose, hemicellulose and lignin. Hemicellulose and cellulose constitute the carbohydrate portion of lignocellulose. These are polymers of sugars (pentoses and hexoses). Lignin is a macromolecule that is rich in phenolic units. Lignocellulosic biomass is defined as, for example, the products that are obtained from forestry operations and the sub-products that are obtained from agriculture, such as straw as well as certain dedicated plants with a high agricultural yield.

The production of chemical products from lignocellulosic biomass makes it possible both to reduce the energy dependency relative to petroleum and to protect the environment through the reduction of greenhouse gas emissions without using resources designed for food uses.

The direct transformation of lignocellulosic biomass or cellulose into chemical products or intermediate products, and in particular into hydroxyacetone and into propylene glycol, is a particularly advantageous method. Direct transformation is defined as the transformation of a stage of lignocellulosic biomass or cellulose, optionally pretreated, into upgradable products, and in particular into hydroxyacetone and into propylene glycol.

Hydroxyacetone, or acetol, has as its chemical formula $C_3H_6O_2$, and its structure is reflected in its systematic name, 1-hydroxy-propanone. Hydroxyacetone is used as, for example, a chemical intermediate product, and as a monomer for the synthesis of polyols, but also as a chemical solvent.

The production of hydroxyacetone can be done by a chemical method or by a biological method. The chemical methods for the production of hydroxyacetone that are known to one skilled in the art are carried out via the transformation of petrochemical intermediate products such as the hydration of propylene. The oxidation of 1,2-propanediol produced by biological means can also lead to the formation of hydroxyacetone.

The propylene glycol or propane-1,2-diol has $C_3H_8O_2$ as its chemical formula, and its structure is reflected in its systematic name, 1,2-dihydroxypropane. The applications of propylene glycol are numerous and diverse: for example, its use as food additive, emulsifier, intermediate product of unsaturated polyesters, but also that of cooling liquid or its use in the textile industry will be cited.

The production of propylene glycol is implemented industrially by hydration of propylene oxide.

The upgrading of the lignocellulosic biomass or the cellulose that is contained in the biomass by heterogeneous catalysis is described in the literature. The patent application EP-A1-B 2011 569 describes the hydrolysis of the cellulose into sorbitol or into mannitol, in an aqueous medium with heterogeneous metallic catalysts.

The patent application WO 03/035582 describes the hydrogenolysis of sorbitol at 200° C. by using (Ni, Re)/C catalysts, which leads to yields of 30% of diols such as ethylene glycol and propylene glycol.

The production of propylene glycol by treatment of cellulose under hydrothermal conditions in the presence of Ru/C heterogeneous catalysts is observed by Luo et al. (Angew. [Applied] Chem. Int. Ed. 2007, 46, 7636-7639). The maximum carbon yield obtained in propylene glycol is 2.2% by weight for reactions conducted at a temperature of 245° C., an $H_2$ pressure of 6 MPa, in an aqueous medium. Under these reaction conditions, the conversion of cellulose is approximately 39%. The production of hydroxyacetone is not reported.

Ji et al. (Angew. Chem. Int. Ed. 2008, 47, 8510-8513) also studied the reaction for transformation of the cellulose in a hydrothermal medium by using catalysts that are based on tungsten carbides with a carbon substrate with nickel as a promoter, promoting good selectivity for ethylene glycol and sorbitol with this type of catalyst. The operating conditions are a temperature on the order of 245° C. and a hydrogen pressure of 6 MPa, in the presence of water. The maximum mass yield of 1,2-propylene glycol is 7.7% for a tungsten carbide-nickel catalyst with a carbon substrate. By using a catalyst of the 2.5% $Pt/Al_2O_3$ type, the mass yield of propylene glycol is 9.3%. The conversion of the cellulose is total in the two cases.

There again, the production of hydroxyacetone is not mentioned.

Likewise, Zhang et al. (Chem. Commun., 2010, 46, 862-864) recently promoted the direct conversion of cellulose into ethylene glycol by tungsten-carbide-based catalysts with substrates of carbon-containing materials of commercial silica. During these experiments, with a temperature on the order of 245° C., and a hydrogen pressure of 6 MPa, in aqueous medium, the maximum mass yield of propylene glycol is 8.4%, the conversion of cellulose is total, and the formation of hydroxyacetone is not observed.

The same research team promoted the conversion of cellulose into ethylene glycol by nickel tungsten catalysts with an SBA-15-type mesoporous silica substrate (Zheng et al., ChemSusChem., 2010, 3, 63-66). Once again, a total conversion of cellulose is obtained with a low maximum mass yield of propylene glycol (on the order of 4%) and without formation of hydroxyacetone.

The U.S. Pat. No. 2,488,722 describes a process for transformation of cellulose into hydroxyacetone and into propylene glycol, in which the cellulose is dissolved in Schweizer's reagent, i.e., in an ammoniacal solution of copper oxide, and then the solution is reduced to form a mixture of isopropyl alcohol, propylene glycol, and hydroxyacetone.

The document Science China Chemistry, 2010, 53, 1476-4780 describes a process for transformation of cellulose into polyols in which the cellulose is hydrogenolyzed at high temperature and high pressure in a basic aqueous medium in the presence of ruthenium for resulting in a mixture of ethylene glycol, propylene glycol, 1,2,5-pentanetriol and acetol.

Finally, processes for thermal and non-catalytic conversions such as pyrolysis or the direct liquefaction of lignocellulose lead to the production of biomass liquefiers. The minority presence of hydroxyacetone is sometimes noted. For example, Patwardhan et al., Bioresource Technology, 2010, 101, 4646-4655 will be cited. Nevertheless, besides their application conditions (temperature, pressure), these non-catalytic processes are very removed from the process that is the object of the invention.

Thus, no process that allows a direct transformation of cellulose or, more broadly, lignocellulose biomass, optionally pretreated, into upgradable products, in particular into hydroxyacetone and into propylene glycol with high selectivity by means of heterogeneous catalysts of the type of those described in this invention was reported in the literature.

SUMMARY OF THE INVENTION

The applicants discovered a process for direct transformation of cellulose, present in the lignocellulosic biomass, optionally pretreated, into hydroxyacetone and into propylene glycol, using a heterogeneous catalyst based on tin oxide and/or antimony oxide, preferably dispersed on a substrate and containing at least one element in the metal state selected from the groups 8 to 11 of the periodic table.

DETAILED DESCRIPTION OF THE INVENTION

The invention relates to a process for transformation of the lignocellulosic biomass or cellulose into hydroxyacetone and into propylene glycol, in which the lignocellulosic biomass or cellulose is brought into contact, under hydrothermal conditions and under a reducing atmosphere, with a heterogeneous catalyst that is based on tin oxide and/or antimony oxide and that contains at least one element in the metal state that is selected from the groups 8 to 11 of the periodic table, said catalyst having Lewis-type acid sites.

In a preferred way, said catalyst is dispersed on a substrate.

The process according to the invention makes it possible to obtain in a selective way a mixture of products comprising hydroxyacetone and propylene glycol in a significant quantity.

During the transformation of the feedstock, it is possible to obtain a mixture of different products comprising in particular glucose, sorbitol, lactic acid, formic acid, levulinic acid, acetic acid, hydroxyacetone, propylene glycol, 2,5-hexanedione, 5-HMF (hydroxymethylfurfural), 1,2-hexanediol, soluble products and oligosaccharides and soluble polymers.

The process makes it possible to obtain high conversions of the reagent and significant selectivities, in particular high yields of hydroxyacetone and propylene glycol, while limiting the formation of oligosaccharides or water-soluble polymers. These conversions and selectivities are obtained only under hydrothermal conditions (presence of water), while operating under reducing atmosphere, and only in the presence of catalysts that are based on tin oxides and/or antimony oxides that have Lewis-type acid properties and that contain an element in the metal state that is selected from the groups 8 to 11. Actually, the solid catalysts for the most part having a Brønsted acidity promote the production of soluble oligosaccharides and/or soluble polymers, exhibiting a lower selectivity in desired chemical intermediate products. In contrast, the catalysts with an oxide base of tin oxides and/or antimony oxide have Lewis-type acid properties and, not containing metal, do not lead to the formation of the desired chemical intermediate products but make it possible to obtain lactic acid selectively.

Thus, the molar yield of hydroxyacetone and propylene glycol is greater than the yield of each of the other products obtained during the transformation of the lignocellulosic biomass and is also greater than the sum of the yields of the different products taken as a whole.

Said substrate is preferably based on oxide(s) preferably selected from among the oxides of aluminum and/or zirconium and/or titanium and/or niobium and/or silicon. Said substrate can also be a carbon-containing substrate.

The content of Lewis-type acid sites of the catalyst is preferably higher than 50% of the total acid site content. The term total acid site content is understood to mean the sum of Lewis acid sites and Bronsted acid sites.

The use of these catalysts makes it possible to obtain directly upgradable products, in particular hydroxyacetone and propylene glycol, of high selectivity while limiting the production of oligosaccharides and soluble polymers.

The process according to this invention makes it possible also to improve the conversion of the cellulose that is present in the lignocellulosic biomass.

The Feedstock

The lignocellulosic biomass essentially consists of three natural components that are present in variable amounts according to the origin thereof: cellulose, hemicellulose, and lignin.

Cellulose $(C_6H_{10}O_5)_n$ represents the major portion (40-60%) of the composition of the lignocellulosic biomass. This is a semi-crystalline linear homopolymer of glucose. Cellulose is insoluble in water at ambient temperature and pressure.

Hemicellulose is the carbohydrate that is second in quantity after cellulose and constitutes 20 to 40% by weight of the lignocellulosic biomass. In contrast to cellulose, this polymer consists for the most part of monomers of pentoses (cyclic compounds with five atoms) and hexoses (cyclic compounds with 6 atoms). Hemicellulose is an amorphous heteropolymer with a degree of polymerization that is lower than that of cellulose (30-100).

Lignin is an amorphous macromolecule that is present in the lignocellulosic compounds in variable proportions according to the origin of the material (straw ~15%, wood: 20-26%). Its function is mechanical reinforcement, hydrophobization, and support of plants. This macromolecule that is rich in phenolic units can be described as a resultant of the combination of three monomer units of the propyl-methoxyphenol type. Its molar mass varies from 5,000 g/mol to 10,000 g/mol for hardwoods and reaches 20,000 g/mol for softwoods.

The lignocellulosic raw material can consist of wood or plant waste. Other nonlimiting examples of lignocellulosic biomass material are waste from agricultural operations (straw, grasses, stems, pits, shells, . . . ), waste from forestry operations (initial cutting products, bark, sawdust, chips, scraps, . . . ), products from forestry operations, dedicated crops (short-rotation shrubs), waste from the food-processing industry (waste from the industry of cotton, bamboo, sisal, banana, corn, switchgrass, alfalfa, coconut, bagasse, . . . ), household organic waste, waste from wood transformation plants, scrap wood from construction, and paper, which may or may not be recycled.

The feedstock that is used in the process according to the invention is lignocellulosic biomass or cellulose. The cellulose that is used may be crystalline, partially amorphous, or amorphous.

The lignocellulosic biomass feedstock can be used in its raw form, i.e., is made up in its entirety of these three cellulose, hemicellulose and lignin components. The raw biomass generally comes in the form of fibrous residues or powder. In general, it is ground or shredded to allow its transport.

The lignocellulosic biomass feedstock can also be used in its pretreated form, i.e., in a form that contains at least one cellulosic portion after extraction of lignin and/or hemicellulose.

The biomass preferably undergoes a pretreatment so as to increase the reactivity and the accessibility of cellulose within the biomass before its transformation. These pretreatments are of a mechanical, thermochemical, thermo-mechanical-chemical and/or biochemical nature and bring about the partial or total decrystallization of cellulose, the total or partial solubilization of hemicellulose and/or lignin, or the partial hydrolysis of hemicellulose following the treatment.

The lignocellulosic biomass feedstock can also be pretreated so as to be in the form of water-soluble oligomers. These pretreatments are of a mechanical, thermochemical, thermo-mechanical-chemical and/or biochemical nature. They bring about the decrystallization and the solubilization of the cellulose in the form of water-soluble oligomers.

The mechanical treatments go beyond simple shredding because they modify the chemical structure of the components. They improve the accessibility and the reactivity of cellulose by its partial or total decrystallization and by the increase in the exchange surface area. The mechanical treatments include the reduction of the size of fibers or elementary particles, for example by chipping the biomass with a cutter, by grinding the biomass (adjustment of the grain size), destructuring chips on a press, or defibration by chip abrasion, after preheating. The mechanical treatments can be performed in decentralized mode close to where the biomass is produced or in a centralized mode that directly feeds the transformation.

The thermochemical treatments include the baking of the biomass at high temperature (150-170° C.) in a dilute acid medium (primarily sulfuric acid, but also phosphoric acid, acetic acid, or formic acid), in an alkaline medium (soda, sulfites, lime, . . . ) or in an oxidizing medium (wet oxidation with air or oxygen; peroxide in an alkaline medium; peracetic acid). The other thermochemical treatments include treatments with solvents (hot ethanol) or roasting that can be defined as pyrolysis at moderate temperature and with a controlled dwell time because it is accompanied by partial destruction of the lignocellulosic material. The known technologies for roasting are, for example, the rotary kiln, the moving bed, the fluidized bed, the heated endless screw, and the contact with metal balls that provide heat. These technologies can optionally use a gas that circulates in co-current or counter-current such as nitrogen or any other inert gas under the conditions of the reaction.

The thermo-mechanical-chemical treatments include vapor treatments (vapor explosion also called flash hydrolysis or "steam explosion"), the AFEX (ammonia fiber explosion) treatment with ammonia, or two-screw extrusion with various chemical reagents.

The pretreatment makes it possible to prepare the lignocellulosic biomass by separating the carbohydrate portion of the lignin and adjusting the size of the biomass particles that are to be treated. The size of the biomass particles after pretreatment is generally less than 5 mm, preferably less than 500 microns.

The Catalyst

The catalysts that are used for the transformation of the lignocellulosic biomass or cellulose according to this invention are based on tin oxide and/or antimony oxide, preferably dispersed on the surface of a substrate, and they contain at least one element in the metal state that is selected from the groups 8 to 11 of the periodic table.

In a general manner, the acidity of a catalyst is the resultant of two combined types of acidity: Lewis acidity, characterized by the presence of an electron gap on an atom, and Brønsted acidity, characterized by a capability of giving up a proton. The nature of the acid sites can be characterized by adsorption of pyridine followed by IR spectroscopy in accordance with the method that is described in [M. Guisnet, P. Ayrault, C. Coutanceau, M. F. Alvarez, J. Datka, *J. Chem. Soc., Faraday Trans.* 93, 1661 (1997)].

The solids that are used in the process according to the invention are characterized by superficial acidic properties that are for the most part of the Lewis type.

In a preferred way, the catalyst has a content of Lewis acid sites that is greater than 50% of the total acidity of said solid. The Lewis-type acid sites are associated with the presence of tin and/or antimony radicals that are coordinatively unsaturated but also with radicals that are characteristic of the substrate, such as, for example: $Al^{3+}$, $Zr^{4+}$, $Ti^{4+}$, and $Nb^{5+}$. The Lewis acidity can be characterized by, for example, IR spectroscopy.

The substrate that is used for dispersing tin and/or antimony and a particular element in the metal state can be an oxide, preferably selected from among alumina, zirconia, niobium oxide, titanium oxide, silica, and zeotypes, such as, for example, zeolites, aluminophosphates, mesostructured compounds, by themselves or in a mixture, prepared according to any technique that is known to one skilled in the art. For example, the substrates can be synthesized by precipitation, or sol-gel synthesis followed by a heat treatment. The solids that are obtained have the advantage of being stable, thermally and under hydrothermal conditions.

The substrate can also be a carbon-containing substrate such as, for example, activated carbons, carbon black, carbon-containing microporous or mesoporous solids, such as, for example, carbon nanotubes, or carbon fibers. The carbon-containing substrates are prepared according to any technique that is known to one skilled in the art. The carbon-containing substrates can undergo a treatment so as to modify, for example, their properties of acidity, hydrophobicity, and texture. For example, the heat treatments, oxidizing treatments and reducing treatments . . . can be cited.

The tin and/or antimony content is between 1 to 100% by weight, preferably between 1 and 50% by weight, preferably between 1 and 30%, and even more preferably between 1 and 20% by weight, with the percentages being expressed in terms of % by weight of metal relative to the total mass of catalyst.

The precursors of tin or antimony are selected from among hydrides, halides (chlorides, bromides, iodides, fluorides), oxides, sulfides, or organometallic compounds respectively of tin or antimony. The tin chlorides are the usual precursors. The use of tin chloride in solution in hydrochloric acid is preferred. Among the tin organometallic compounds, tin alkyls and more particularly tetrabutyltin will be cited.

The preparation of catalysts based on tin oxide and/or antimony oxide can be carried out according to any technique that is known to one skilled in the art, such as, for example, the ion exchange, the dry impregnation, or the excess impregnation. One preparation method consists of an impregnation of a stannic acid solution and/or antimony oxide and the substrate, preferably based on oxide, followed by calcination.

The presence of tin and/or antimony on the substrate brings about the formation of tin oxide and/or antimony oxide.

The element in the metal state that is present in the catalyst that is used according to this invention is a metal that is selected from among a metal of the groups 8 to 11 of the periodic table. It is selected from among Fe, Co, Ni, Ru, Rh, Pd, Os, Ir, Pt, or Cu, Au, Ag. In a preferred manner, the element is selected from among Pt, Ni, Ru, or Cu. In a more preferred manner, the element is selected from among Pt, Ni and Ru. In a very preferred manner, it is platinum.

The metal precursors can be, without limiting their origin, organometallic complexes, metal salts. For the salts of metals, for example, metal chlorides and metal nitrates will be cited.

The introduction of metal can be done by any technique that is known to one skilled in the art such as, for example, ion exchange, dry impregnation, excess impregnation, vapor phase deposition, etc. The introduction of metal can be done before or after the shaping of the catalyst that is based on tin oxide and/or antimony oxide, dispersed on a substrate.

The content by weight of the metal element that is introduced is advantageously between 0.01 and 10% by weight, and preferably between 0.05 and 5% by weight relative to the total mass of the catalyst.

The stage for introduction of the metal element is followed by a heat treatment stage. The heat treatment is advantageously carried out between 300° C. and 700° C. The heat treatment stage can be followed by a temperature reduction treatment. The reducing heat treatment is advantageously carried out at a temperature of between 200° C. and 600° C. under a stream of hydrogen or under hydrogen atmosphere.

The reduction stage can be carried out in-situ, i.e., in the reactor where the reaction takes place, before the introduction of the reaction feedstock. The reduction can also be carried out ex-situ.

The catalysts that are used in this invention can be in the form of powder, extrudates, balls or pellets. The shaping can be done before or after the metal and/or tin and/or antimony is/are introduced.

At the end of the heat treatments and/or reducing treatments, the presence of alloy formed between the tin oxide and/or the antimony oxide and the element in the metal state selected from the groups 8 to 11 of the periodic table can be observed. For example, the presence of platinum/tin alloy and/or platinum/antimony alloy can be observed.

The catalysts that are used in this invention are characterized by the techniques that are known to one skilled in the art.

The catalyst that is used according to the invention is stable and can be regenerated, i.e., it does not undergo lixiviation during the reaction. At the end of a stage for washing or combustion of the hydrocarbon radicals that are deposited on the catalyst after reaction, the catalyst has the same initial catalytic performance levels.

Transformation Process

The process for transformation of the lignocellulosic biomass or cellulose according to the invention comprises the reaction in a water-containing medium in the presence of the catalytic composition according to the invention.

Water-containing medium refers to the conventional liquid media like alcohols, such as, for example, methanol or ethanol, and water, and the non-conventional media, like ionic liquids or supercritical media of liquid-type density.

The content by mass of water in the medium is generally greater than 1%. Preferably, the medium is water.

The process for transformation of the lignocellulosic biomass or the cellulose according to the invention is carried out under reducing atmosphere, preferably under hydrogen atmosphere. The hydrogen can be used in pure form or in a mixture.

The process is carried out at temperatures of between 160° C. and 250° C., preferably between 175° C. and 250° C., and at a pressure of between 0.5 MPa and 20 MPa, preferably between 2 MPa and 10 MPa.

In general, the reaction can be performed according to different embodiments. Thus, the reaction can be implemented intermittently or continuously, for example in a fixed bed. It is possible to operate with a closed or semi-open reactor.

The catalyst is introduced into the reactor at a rate of a quantity that corresponds to a biomass/catalyst mass ratio of between 1 and 1,000, preferably between 1 and 500, preferably between 1 and 100, preferably between 1 and 50, and even preferably between 1 and 25.

The catalyst that is introduced into the reactor can undergo a reducing heat treatment stage before the introduction of the reaction feedstock. The reducing heat treatment is carried out at a temperature of between 200° C. and 600° C. under a stream of hydrogen or under hydrogen atmosphere.

The biomass is introduced into the process at a rate of a quantity that corresponds to a (water-containing medium)/biomass mass ratio of between 1 and 1,000, preferably between 1 and 500, and even preferably between 5 and 100. The dilution rate of the biomass is therefore between 1:1 and 1:1,000, preferably between 1:1 and 1:500, and even preferably between 1:5 and 1:100.

If a continuous process is selected, the mass speed per hour (catalyst mass/mass feedstock flow rate) is between 0.01 and 5 $h^{-1}$, preferably between 0.02 and 2 $h^{-1}$.

The Products that are Obtained and their Mode of Analysis

After the reaction, the reaction medium is sampled and centrifuged. The reaction liquid is next analyzed by high-pressure liquid chromatography (HPLC) by using refractometry for determining the content of conversion products of the aqueous solution.

The products of the reaction are water-soluble. They consist of monosaccharides and their derivatives, oligosaccharides, but also soluble polymers that are formed by successive combinations of the derivatives of monosaccharides.

Monosaccharides refer to the simple sugars (hexoses, pentoses) that are produced by complete depolymerization of cellulose and/or hemicellulose, in particular glucose, mannose, xylose, fructose, . . . .

Monosaccharide derivatives refer to the products that can be obtained by dehydration, isomerization, reduction or oxidation:

Alcohol sugars, alcohols and polyols: in particular sorbitol, xylitol, glycerol, ethylene glycol, propylene glycol, ethanol, hydroxyacetone, . . . , Ketones, hexane-diones: 2,5-hexanedione, hydroxyacetone, . . . , Carboxylic acids and their esters, lactones: formic acid, levulinic acid, alkyl levulinates, lactic acid, alkyl lactates, glutaric acid, alkyl glutarates, 3-hydroxypropanoic acid, 3-hydroxybutyrolactone, γ-butyrolactone, Cyclic ethers: for example, tetrahydrofuran (THF), methyltetrahydrofuran (Me-THF), dicarboxylic acid furan, 5-(hydroxymethyl)furfural, . . . .

Oligosaccharides refer to a carbohydrate that has as its composition $(C_6H_{10}O_5)_n$, where n is greater than 1, obtained by partial hydrolysis of cellulose, or hemicellulose, or starch.

Soluble polymers refer to all of the products that are obtained from condensation between monosaccharides, oligosaccharides and/or derivatives of monosaccharides.

The quantity of water-soluble reaction products (monosaccharides and derivatives, oligosaccharides, soluble polymers) is determined by the COT [TOC] (Total Organic Carbon) analysis that consists of the measurement of carbon in solution. The quantity of monosaccharides and their derivatives is determined by HPLC analyses.

The conversion is defined as the percentage of solubilization of the biomass or cellulose and is calculated according to the following equation:

$$C=100*C_{solubilized}/C_{initial}$$

in which $C_{solubilized}$ represents the quantity of solubilized carbon that is analyzed by TOC (mg), and $C_{initial}$ represents the quantity of carbon at the beginning of the reaction that is contained in the biomass or solid cellulose.

The molar yields of glucose derivatives are calculated by means of HPLC analysis. Each compound is corrected by the carbon atom number contained in the glucose unit.

The molar yields of a derivative i are calculated as follows:

$$Rdt_i=100*(nC_{Pi}/6)*(P_i/Glu_o)$$

where $nC_{Pi}$ represents the number of carbon atoms of the derivative i, Pi represents the number of moles of the product $P_i$, and $Glu_0$ represents the number of moles of glucose units contained in the biomass or cellulose at the beginning of the reaction.

The formations of oligosaccharides and soluble polymers correspond to a loss of carbon. This loss of carbon is deduced from TOC and HPLC analyses. The yield of oligosaccharides and soluble polymers is calculated according to the following equation:

$$Rdt_{olig}=C-\Sigma rdt_i$$

where C represents the conversion of the cellulose and $\Sigma rdt_i$ represents the sum of molar yields of all of the monosaccharides and their derivatives that are analyzed by HPLC.

EXAMPLES

Example 1

Preparation of the Catalyst C1 that is Based on Tin Oxide, Dispersed on a Substrate that is Based on Alumina Oxide (not in Accordance with the Invention)

The catalyst is prepared by using aluminum hydroxide and pentahydrated tin chloride as raw material. 5.0 g of aluminum hydroxide is subjected to impregnation with nascent humidity with an aqueous solution of tin chloride (3.0 g of $SnCl_4$, $5H_2O$ in 4.5 g of water). The solid that is obtained is then dried at 80° C. for 24 hours.

Next, the solid is calcined under a flow of dry air at the temperature of 700° C. for 3 hours. At the end of these treatments, the catalyst C1 contains 15% by weight of tin. The proportion of Lewis acid sites of the catalysts C1 is greater than 90%.

Example 2

Preparation of the Catalyst C2 that is Based on Tin Oxide, Dispersed on a Substrate that is Based on Alumina Oxide and Platinum (in Accordance with the Invention)

1 g of the catalyst C1 is treated under vacuum for 1 hour at 100° C. An aqueous solution of hexachloroplatinic acid $H_2PtCl_6.xH_2O$ at 8% by weight (1.3 ml, 0.525 g) is then added to the catalyst C1. The mixture is stirred for one hour. The aqueous solution is evaporated. In the first place, the solid that is obtained is dried in the oven at 110° C. for 24 hours, and then treated thermally under a stream of dry nitrogen at the temperature of 550° C. for two hours and then reduced under a stream of hydrogen at 300° C. for two hours.

The thus obtained catalyst C2 contains 2.2% by weight of platinum and 15% by weight of tin. The proportion of Lewis acid sites of the catalysts C2 is greater than 90%.

Example 3

Preparation of a Platinum-Based Catalyst C3 with a Silica Substrate (not in Accordance with the Invention)

The raw material that is used is the commercial substrate $SiO_2$ Alfa Aesar. Typically, an aqueous solution of tetramine platinum (1.3 ml; 0.171 g) is added at ambient temperature to silica (1 g) that was previously desorbed under vacuum (1 hour, 100° C.). The mixture is stirred for one hour and then is next evaporated. The solid that is obtained is then brought to dry in the oven at 110° C. for 24 hours. Then, the catalyst is calcined under a stream of dry nitrogen at the temperature of 500° C. for two hours, and then reduced under a stream of hydrogen at 300° C. for two hours.

The catalyst C3 that is obtained contains 1.6% by weight of platinum.

Example 4

Transformation of Cellulose Using the Catalysts that are Prepared in Examples 1, 2 and 3

This example relates to the conversion of cellulose from the catalysts C1, C2 and C3 for the production of upgradable products C3, and in particular hydroxyacetone and propylene glycol.

65 ml of water, 1.6 g of Avicel® cellulose (70% crystallinity), and 0.68 g of the catalyst C1, C2 or C3 are introduced into a 100-ml autoclave. The autoclave is heated to 190° C., and a hydrogen pressure of 5 MPa is introduced. After 24 hours of reaction, the reaction medium is sampled and centrifuged. The reaction liquid is next analyzed by high-pressure liquid chromatography (HPLC) by using refractometry for determining the content of conversion products of the aqueous solution.

The conversion of the cellulose is also carried out in the absence of catalyst, by way of comparison.

The results that are obtained are referenced in Table 1.

TABLE 1

Conversion of Cellulose. Yields of Lactic Acid, Hydroxyacetone, Propylene Glycol, and Total Yield of $C_3$ Products.

| Catalyst | Cellulose Conversion (%) | Molar Yield (%) | | | | |
| --- | --- | --- | --- | --- | --- | --- |
| | | Lactic Acid (%) | Hydroxy-acetone (HA) (%) | Propylene Glycol (PG) (%) | Sum of the HA and PG Products | Sum of the Other Products |
| Without Catalyst | 32 | 4 | 2 | 0 | 2 | 30 |
| AlSn (C1, Example 1) | 44 | 23 | 3 | 0 | 3 | 41 |
| Pt/AlSn (C2, Example 2) | 63 | 3 | 30 | 13 | 43 | 20 |
| Pt/SiO$_2$ (C3, Example 3, Anomalous) | 28 | 1 | 7 | 1 | 8 | 20 |

For the catalyst C1, AlSn, not in accordance with the invention, the quantity of hydroxyacetone that is formed represents 3 mol % of the quantity of initial cellulose, with 3 mol % of hydroxyacetone molecules and propylene glycol. The conversion is 44%. The propylene glycol yield is zero.

For the catalyst C3, Pt/SiO$_2$, not in accordance with the invention, the quantity of hydroxyacetone that is formed represents 7 mol % of the quantity of initial cellulose. The quantity of hydroxyacetone and propylene glycol produced is 8 mol %. The conversion of cellulose is 28%.

The combination of a metal phase Pt and a substrate with a Lewis acidity brought by tin proves effective in comparison with the combination of platinum and a substrate without Lewis acidity (catalyst C2 vs. catalyst C3). A molar yield of hydroxyacetone that is four times higher in the presence of tin and platinum is observed. The propylene glycol yield is also higher to a large extent. The conversion of cellulose is doubled.

In addition, the combination of platinum and a tin-containing substrate shows itself to be effective in comparison with a tin-containing catalyst without platinum. An increase in the total conversion of 19 points and in the selectivity of oxidized $C_3$ molecules of 21 points in the case of tin-containing alumina with or without the presence of platinum is observed. A difference in selectivity is observed during the addition of platinum. In the absence of platinum, high selectivity is obtained in lactic acid. In the presence of platinum, high selectivity of hydroxyacetone and propylene glycol is obtained.

Thus, these examples demonstrate the production of oxidized $C_3$ molecules with high yield and selectivity by direct transformation of cellulose via tin- and platinum-based heterogeneous catalysts.

Example 5

(Not in Accordance with the Invention): Transformation of Cellulose Using the Catalyst C2 Prepared in Example 2 at a Temperature of 150° C.

This example relates to the conversion of cellulose from the catalyst C2 for the production of upgradable C3 products, and in particular hydroxyacetone and propylene glycol.

65 ml of water, 1.6 g of Avicel® cellulose (70% crystallinity), and 0.68 g of catalyst C2 are introduced into a 100-ml autoclave. The autoclave is heated to 150° C., and a hydrogen pressure of 5 MPa is introduced. After 24 hours of reaction, the reaction medium is sampled and centrifuged. The reaction liquid is next analyzed by high-pressure liquid chromatography (HPLC) by using refractometry for determining the content of conversion products of the aqueous solution.

The results that are obtained are referenced in Table 2.

TABLE 2

Conversion of Cellulose. Yields of Lactic Acid, Hydroxyacetone, Propylene Glycol, and Total Yield of $C_3$ Products.

| Catalyst | Cellulose Conversion (%) | Molar Yield (%) | | | | |
| --- | --- | --- | --- | --- | --- | --- |
| | | Lactic Acid (%) | Hydroxy-acetone (HA) (%) | Propylene Glycol (PG) (%) | Sum of the HA and PG Products | Sum of the Other Products |
| Pt/AlSn (C2, Example 2) | 5 | 0.2 | 2.5 | 1 | 3.5 | 1.5 |

The process according to the invention that is implemented at a temperature of 150° C. does not make it possible to obtain a high yield in hydroxyacetone and propylene glycol. Furthermore, the conversion into cellulose is 5%.

Example 6

(In Accordance with the Invention): Transformation of Cellulose Using the Catalyst C2 Prepared in Example 2

This example relates to the conversion of cellulose from the catalyst C2 for the production of upgradable C3 products, and in particular hydroxyacetone and propylene glycol.

65 ml of water, 1.6 g of Avicel® cellulose (70% crystallinity), and 0.68 g of catalyst C2 are introduced into a 100-ml autoclave. The autoclave is heated to 190° C., and a hydrogen pressure of 8 MPa is introduced. After 24 hours of reaction, the reaction medium is sampled and centrifuged. The reaction liquid is next analyzed by high-pressure liquid chromatography (HPLC) by using refractometry for determining the content of conversion products of the aqueous solution.

The results that are obtained are referenced in Table 3.

TABLE 3

Conversion of Cellulose. Yields of Lactic Acid, Hydroxyacetone, Propylene Glycol, and Total Yield of $C_3$ Products.

| | | | Molar Yield (%) | | | |
|---|---|---|---|---|---|---|
| Catalyst | Cellulose Conversion (%) | Lactic Acid (%) | Hydroxy-acetone (HA) (%) | Propylene Glycol (PG) (%) | Sum of the HA and PG Products | Sum of the Other Products |
| Pt/AlSn (C2, Example 2) | 75 | 3 | 15 | 38 | 53 | 22 |

The use of the catalyst C2 according to the invention makes it possible to obtain a high molar yield of hydroxyacetone and propylene glycol. The propylene glycol yield is also greater, to a large extent, than those observed by using catalysts that are not in accordance with the invention (C1 and C3). The conversion of the cellulose is 75%.

Example 7

(In Accordance with the Invention): Preparation of a Tin-Oxide-Based Catalyst C4, Dispersed on a Substrate Based on Aluminum Oxide and Ruthenium Oxide 1 g of catalyst C1 is treated under vacuum for 1 hour at 100° C. An aqueous solution of $RuCl_3$ is then added to the catalyst C1. The mixture is stirred for one hour. The aqueous solution is evaporated. In the first place, the solid that is obtained is dried in the oven at 110° C. for 24 hours, and then treated thermally under a stream of air at the temperature of 300° C. for two hours.

The thus obtained catalyst C4 contains 2% by weight of ruthenium and 15% by weight of tin. The proportion of Lewis acid sites of the catalysts C2 is greater than 90%.

Example 8

(In Accordance with the Invention): Preparation of a Tin-Oxide-Based Catalyst C5, Dispersed on a Substrate that is Based on Aluminum Oxide and Copper Oxide 1 g of catalyst C1 is treated under vacuum for 1 hour at 100° C. An aqueous solution of $Cu(NO_3)_2$ is then added to the catalyst C1. The mixture is stirred for one hour. The aqueous solution is evaporated. In the first place, the solid that is obtained is dried in the oven at 110° C. for 24 hours, and then treated thermally under a stream of air at the temperature of 300° C. for two hours.

The thus obtained catalyst C5 contains 10% by weight of copper and 15% by weight of tin. The proportion of Lewis acid sites of the catalysts C2 is greater than 90%.

Example 9

Transformation of Cellulose that Uses the Catalyst that is Prepared from Catalysts C4 and C5

This example relates to the conversion of cellulose from the catalysts C4 and C5 in accordance with the invention for the production of upgradable products C3, and in particular hydroxyacetone and propylene glycol.

65 ml of water, 1.6 g of Avicel® cellulose (70% crystallinity), and 0.68 g of catalyst C1, C2 or C3 are introduced into a 100-ml autoclave. The autoclave is heated to 190° C., and a hydrogen pressure of 5 MPa is introduced. After 24 hours of reaction, the reaction medium is sampled and centrifuged. The reaction liquid is next analyzed by high-pressure liquid chromatography (HPLC) by using refractometry for determining the content of conversion products of the aqueous solution.

The results that are obtained are referenced in Table 4.

TABLE 4

Conversion of Cellulose. Yields of Lactic Acid, Hydroxyacetone, Propylene Glycol, and Total Yield of $C_3$ Products.

| | | | Molar Yield (%) | | | |
|---|---|---|---|---|---|---|
| Catalyst | Cellulose Conversion (%) | Lactic Acid (%) | Hydroxy-acetone (HA) (%) | Propylene Glycol (PG) (%) | Sum of the HA and PG Products | Sum of the Other Products |
| Ru/AlSn | 50 | 5 | 13 | 8 | 21 | 24 |
| Cu/AlSn | 37 | 2 | 12 | 9 | 21 | 16 |

The use of the catalysts C4 and C5 according to the invention makes it possible to obtain a high molar yield of hydroxyacetone and propylene glycol as well as a high cellulose conversion.

The invention claimed is:
1. Process for transformation of lignocellulosic biomass or cellulose into hydroxyacetone and propylene glycol, in which the lignocellulosic biomass or cellulose is brought into contact, under hydrothermal conditions and under a reducing atmosphere, with a heterogeneous catalyst that is based on tin oxide and/or antimony oxide and that contains at least one element in the metal state that is selected from among Pt, Ni, Ru, Cu, with said catalyst having Lewis-type acid sites, said content of Lewis acid sites being greater than 50% of the total acid site content, and with said process being carried out at a temperature of between 160 and 250° C., and at a pressure of between 0.5 and 20 MPa.

2. Process according to claim 1, in which said catalyst is dispersed on a substrate.

3. Process according to claim 1, in which the content by weight of the element in the metal state is between 0.01 and 10% by weight relative to the total mass of the catalyst.

4. Process according to claim 1, in which the content of tin and/or antimony is between 1 and 100% by weight, relative to the total mass of the catalyst.

5. Process according to claim 2, in which the oxide-based substrate is selected from among the group that is formed by the oxides of aluminum and/or zirconium and/or titanium and/or niobium and/or silicon.

6. Process according to claim 2, in which the substrate is a carbon-containing substrate, selected from among activated carbons, carbon black, or carbon-containing microporous or mesoporous solids.

7. Process according to claim 1, in which the catalyst is synthesized by ion exchange or by impregnation, followed by a heat treatment.

8. Process according to claim 1, in which the transformation is implemented in a water-containing medium, with said medium being selected from among the group that is formed by a liquid medium, an ionic liquid, and a supercritical medium of liquid-type density.

9. Process according to claim 8, in which the content by mass of water is greater than 1%.

10. Process according to claim 1, in which the reducing atmosphere is a hydrogen atmosphere, in pure form or in a mixture.

11. Process according to claim 1, in which the transformation is carried out at a temperature of between 175 and 250° C., and at a pressure of between 2 and 10 MPa.

12. Process according to claim 1, in which the catalyst is introduced with a biomass/catalyst mass ratio of between 1 and 1,000.

13. Process according to claim 1, in which the catalyst undergoes a reducing heat treatment stage at a temperature of between 200 and 600° C. under a stream or atmosphere of hydrogen prior to the introduction of the lignocellulosic biomass into the reactor.

14. Process according to claim 1, in which the lignocellulosic biomass or cellulose is introduced with a (water-containing medium)/biomass mass ratio of between 1 and 1,000.

15. Process according to claim 1, characterized in that it is implemented intermittently or continuously.

16. Process according to claim 15, wherein it is implemented continuously with a mass speed per hour of between 0.01 and 5 $h^{-1}$.

* * * * *